United States Patent [19]

Rowe et al.

[11] 4,059,967
[45] Nov. 29, 1977

[54] PROCESS FOR FREEZING BLOOD PLATELETS

[75] Inventors: Arthur W. Rowe, Stamford, Conn.; George Dayian, Albany, N.Y.

[73] Assignee: The Community Blood Council of Greater New York, Inc., New York, N.Y.

[21] Appl. No.: 659,397

[22] Filed: Feb. 19, 1976

[51] Int. Cl.² .............................................. F25D 17/02
[52] U.S. Cl. .......................................... 62/64; 62/78; 195/1.8; 424/101
[58] Field of Search .................... 195/1.8; 62/62, 78, 62/64; 424/101; 252/40;71

[56] References Cited

U.S. PATENT DOCUMENTS

| 3,303,662 | 2/1967 | Moline et al. | 62/62 |
| 3,439,510 | 4/1969 | Gray | 62/78 |
| 3,729,947 | 5/1973 | Higuchi | 62/62 X |
| 3,758,382 | 9/1973 | Knorpp | 195/1.8 |
| 3,875,754 | 4/1975 | Faust et al. | 62/64 |
| 3,940,943 | 3/1976 | Sikes et al. | 62/64 |

Primary Examiner—Ronald C. Capossela
Attorney, Agent, or Firm—Burgess, Dinklage & Sprung

[57] ABSTRACT

A frozen proteinaceous mass comprising blood platelets coated with glycerol-glucose, the frozen mass prepared by a process comprising:
  A. Contacting blood platelets with an aqueous saline solution containing 4 to 7 weight percent glycerol and glucose 2 to 6 weight percent in an at least 5 : 1 volume to volume solution : platelet ratio;
  B. Removing supernatant liquid;
  C. Concentrating platelets to about 20 mg platelets protein per ml.
  D. Thereafter freezing the platelets at a rate of at least 20° C per minute.

13 Claims, No Drawings

PROCESS FOR FREEZING BLOOD PLATELETS

BACKGROUND OF THE INVENTION

1. Field of the Invention

This invention relates to a process for preserving blood platelets for clinical use and to a frozen concentrate containing blood platelets. More especially, this invention is directed to a process for freezing blood platelets by contacting them with an aqueous saline solution containing glycerol and glucose and freezing the same rapidly, following removal of supernatant liquid, at a rate of at least 20° C per minute. This invention is particularly concerned with the intact proteinaceous mass resulting from the thawing of the concentrated blood platelets which mass can be used directly without glycerol removal for infusion into a recipient for the purpose of effecting hemostasis.

2. Discussion of the Prior Art

The growing need for human platelets in clinical medicine and the relatively short period during which they can be stored emphasized the potential usefulness of a method for their cryopreservation. These platets are in such increased demand and the increase is steadily upwards. For instance, one major metropolitan blood center has increased the number of units prepared from 56,370 in 1970 to 105,200 in 1974.

Platelets are known to be extremely sensitive to processing and can readily be rendered inactive during a freezing technique. A number of investigators have looked to the use of dimethyl sulfoxide (DMSO) as a cryopreservative agent for the platelets. The general procedure has been to apply a solution of dimethyl sulfoxide to the platelets to preserve the same during a slow freezing operation. When the platelets are to be used the frozen mass is thawed. However the dimethyl sulfoxide must then be removed from the mass.

The toxicity and odor associated with dimethyl sulfoxide preclude its use unless these platelets are washed to remove the DMSO prior to transfusion. Hence, researchers have looked to other materials as cryopreservative agents.

One pair of researchers has looked to the use of glycerol as a cryopreservative agent. It has been proposed to treat the platelets with a 12% glycerol solution and to freeze the same quite slowly at a rate of about 1° C per minute. Thus Cohen and Gardner reported in New England Journal of Medicine 274 1400–1407 (1966) the freezing of platelets in 12% glycerol at a slow rate of cooling. This resulted in a relatively low recovery of platelets and there has been observed difficulties in the removal of glycerol from the platelet mass prior to transfusion. Other researchers (Dayian, G. and Rowe, A. W, Cryobiology 6, 579 (1970) observed that 12% glycerol causes extensive damage to platelet lysosomes and this platelet injury is further aggravated by freezing.

It has therefore become desirable to provide an alternative to the DMSO cryopreservative agent and to provide an acceptable means for the freezing of platelets. It has become desirable particularly to provide a process for the freezing of blood platelets by an agent which does not cause platelet damage either by its application to the platelets or during the subsequent freezing operation. More especially, it has become desirable to provide a process for the freezing of blood platelets by the use of a cryopreservative agent which is compatible with the platelets and does not have to be removed prior to transfusion of the platelet mass into a recipient.

SUMMARY OF THE INVENTION

The above objects are provided in accordance with the present invention. The present invention contemplates a process for preserving blood platelets which comprises:

A. Contacting said platelets with an aqueous saline solution containing 4 to 7 weight percent glycerol in at least 5 : 1 volume solution to volume platelet ratio;

B. Removing supernatant liquid therefrom; and

C. Thereafter freezing said platelets at a rate of 20° to 40° C per minute.

It has been found that a dilute solution of glycerol < 5% (w/v) has virtually no lasting adverse affect upon the platelets and the same can be treated without harm. More especially, the freezing operation can take place at a substantially faster rate than was heretofore believed. In fact the freezing of the platelets can be accomplished at a rate of at least 20° C per minute and up to 40° C per minute. It has been found that the frozen mass when thawed can be introduced without any glycerol removal directly into a recipient to effect hemostasis. In vitro assays of frozen - thawed platelets, frozen pursuant to the present invention indicate that they compare favorably with fresh platelets when measured by certain viability criteria.

In performing the process it is necessary that the aqueous saline solution contain glucose (dextrose). It is preferred that the dextrose be present in a concentration of 2 to 6 weight percent. This glycerol-glucose mixture functions especially well as a cryopreservative agent and permits the transfusion of the thawed platelets without prior washing of the glycerol.

In conducting the process the platelets are initially contacted with 4 to 7 weight percent glycerol solution, preferably 5 to 6 weight percent glycerol solution. The glycerol-glucose solution is employed in a high excess, at least 5 : 1 and preferably 10–45 : 1 volume solution to volume platelet ratio. After the platelets have been so contacted the mass is subjected to centrifugation to form a concentrated mass of platelets. The supernatant liquid is then removed leaving a concentrated proteinaceous mass. Generally speaking, there should be about 20 mgs. platelet protein per ml. of mass. The composition is then ready for freezing.

Freezing is preferably conducted by disposing the concentrated platelet mass between metal sheets so that the platelet mass itself forms a sheet. This facilitates heat transfer during the freezing operation. Freezing is conducted so that the temperature drop is at least 20° C per minute and up to about 40° C per minute. Preferably, the rate of cooling is between 28° and 34° C per minute. Freezing is conducted until the mass reaches a temperature of −80° C or lower. Thereafter, it may be removed from that freezer and stored in liquid nitrogen at −196° C.

When the platelets are desired for use they are thawed by disposing the container containing the same, usually a thin plastic bag in a water bath which is warmed to 40° C. The rate of thaw is fast preferably about 1000° C/min.

The resultant mass can be diluted with plasma and then transfused. The ability to introduce the glycerol containing platelet mass directly into the recipient after dilution with plasma without damage to the recipient is a significant advantage.

When diluted the resultant mass contains 1 to 20 mgs. protein in the form of platelets per ml. of solution. The amount of the platelet mass introduced into the recipient depends upon the size and particularly the weight of the recipient in the species and the purpose for which it is introduced.

In a preferred embodiment of the invention the glycerol-glucose treating solution contains plasma, preferably present in a concentration of 5 to 30% (v/v). The ability to include dextrose with the platelet mass is significant.

The platelet mass of the invention in frozen form therefore contains between 5 and 7 weight percent glycerol, preferably between 2 and 5 weight percent dextrose and 5 to 30% plasma and is characterized by the fact that virtually all of the platelets remain intact and retain the potential to function near or as normal when the mass is thawed by disposing the same in a water bath and warming the same to 40° C at a rate of 1000° C/min.

The invention can be more readily understood and appreciated when reference is made to the examples below.

EXAMPLES

Human platelet-rich plasma was prepared from blood drawn from acid-citrate-dextrose (ACD, NIH Formula A) and its processing was started within 3 hours after donation using unchilled platelet-rich plasma. A volume of acid citrate dextrose equal to 10% of the weight of platelet-rich plasma was injected into the bag in order to lower the pH to about 6.5 and prevent aggregation. The mixture was centrifuged at 400 RPM for 5 minutes in a Sorvall RC-3 centrifuge fitted with the HGL-4 head. The platelet-poor plasma resulting from the centrifugation was separated by use of a Fenwal Plasma Extractor and retained for later use in preparation of the freezing solution and for resuspension of thawed platelets.

The platelet concentrate resulting from the centrifugation was resuspended in a small quantity of residual plasma about 10 ml. by gentle kneading of the bag and 300 ml. of the freezing were added. The freezing solution consisted of a mixture of 90 ml. of autologous platelet-poor plasma and 210 ml. of a solution containing 7.14% (v/v) glycerol, 5.71% (W/V) glucose and 0.9% (W/V) sodium chloride. The final concentration of glycerol was 5% and that of glucose was 4%.

The suspension of the glycerolized platelets was centrifuged and the supernatant liquid was removed. The platelet concentrate was resuspended in some residual freezing solution (approximately 4–5 ml. per unit) in the manner stated above. Air was injected into the bag and the platelet concentrate was removed into a syringe. The platelet concentrate remaining in the bag was removed by two washings with 1.5 ml. each of freezing solution supernatant liquid. The platelet concentrate having a volume of about 7 ml. per unit was injected into a blood freezing bag (UCAR style 0750-2 Union Carbide). The air was removed and the bag was heat-sealed.

The sealed bag was then placed between two aluminum covers having a 0.8 mm. thickness and clamped. The bag containing the platelets was frozen, together with a similar bag containing the freezing solution without platelets, but fitted with a copper-constantan thermocouple. They were placed on a stand in the Linde Biological Freezer (Union Carbide) so that the bags did not touch one another.

A controlled rate of cooling was achieved by the use of the override switch on the Linde Biological Freezer controller and the recorded temperature was observed. Continuous temperature readings were recorded on the Honeywell Electronic 18 recorder. The rate of cooling was not greater than 30° C per minute until the heat of fusion produced a plateau in the curve (approximately −7° C). Up until that point the cooling was at a rate of approximately 10° to 20° C per minute. Thereafter a rate of about 30° C of cooling was continued until the temperature reached −80° C at which point the freezing assembly was transferred into liquid nitrogen for storage.

The frozen platelets were thawed by submersion of the assembly in a 40° C water bath with mild agitation for 20 seconds. If some aggregation occurred the platelets were kneaded by hand until they dispersed. The thawed platelets were immediately reconstituted in 50 ml. of autologous platelet-free plasma and incubated at room temperature until "swirling" was established, an average of 1 to 2 hours.

Several determinations were conducted to determine the extent to which the cryopreservative agent adversely affected the platelets or if the platelets were adversely affected during the freezing process. The following tests were conducted:

Platelet Recovery

The yield of platelets was determined by counting the platelets in a hemocytometer chamber by phase contrast microscopy, according to the method of Brecher and Cronkite, "Morphology and Enumeration of Human Blood Platelets," Journal of Applied Physiology, Vol. 3, page 365 (1950).

Size Distribution

Platelet size distribution patterns were obtained by use of the Coulter Counter Model ZBI, a size distribution analyzer, Model P64 and x-y recorder II. The 70 micron aperture electrode was used with the following counter settings: 1/amplification = ¼, 1/aperture current = 0.177, matching switch = 20K and gain trim = 2.5. Window settings varied from a lower threshold of a 8 to an upper threshold of 100. The count range setting on the analyzer was 4096. Latex particles (Coulter) 2.02 micron diameter were used to calibrate the instrument. Platelets were resuspended in Isoton (Coulter) to give a concentration of about 400,000/ml.

Serotonin Uptake

The uptake of $^{14}C$-serotonin by platelets was studied by the method of Born and Gillson, "Studies on the Uptake of 5-Hydroxy Tryptamine by Blood Platelets," Journal of Physiology, Vol. 146, page 472 (1959). 3-$^{14}C$-5-hydroxytryptamine creatinine sulphate (55mC/m mole, Amersham) was dissolved in 70% alcohol to give a final concentration of 10 micron c/ml. and stored at −20° C. To 4 ml. of platelet suspension was added 0.01 ml. of the $^{14}C$-serotonin and the mixture incubated at 37° C for 30 minutes. Radioactivity was determined on 0.1 ml. samples of platelet suspensions as well as on platelet free aliquots after centrifugation.

Aggregation

ADP-induced aggregation was performed turbudometrically with a Chronolog aggregometer, Born, G.V.R., "Aggregation of Blood Platelets and its Reversal," Nature, Vol. 194, page 927 (1962) and Born, G.V.R. and Cross, N.J., "The Aggregation of Blood Platelets," Journal of Physiology, Vol. 168, page 178 (1963). Thawed reconstituted platelets were incubated with 1 mg/ml of the enzyme, apyrase (Sigma) for 1 hour at 37° C. This treatment restored the sensitivity of the platelets made refractory to ADP-induced aggregation. The mixture was centrifuged at 4500 × g and resuspended in non-acidified heterologous PFP with added calcium chloride (4mM). Aggregation was induced by addition of 200 micromoles ADP to a platelet suspension of about 240,000/mm$^3$.

Clot Retraction

Clot retraction induced by the addition of thrombin was performed according to the method of Bettex-Galland and Luscher in "Thrombosis and Bleeding Disorders. Theory and Methods" (N. U. Bang, F. K. Beller, E. Deutsch and E. F. Mammen, Eds.) page 442, Academic Press, New York (1971) as described for PRP. Platelets were diluted to 180,000/mm$^3$ in 5 ml. of a mixture consisting of 60% plasma, 6mM imidazole-HCl buffer, pH 7.4, 1 mM glucose and 60 mM NaCl. The suspension was preincubated for 5 minutes at 37° C before the addition of 0.5 ml. thrombin (6 units) in 2 mM CaCl$_2$. Incubation was continued at 37° C.

RESULTS

Recovery of Platelets After Freeze-Thawing

After overnight storage in liquid nitrogen, the platelets were thawed and counted by phase microscopy and compared with the number of platelets in the starting platelet-rich plasma. Table 1A set forth below lists the results of 26 preparations performed on a routine basis. Recoveries ranged from 42 to 97% with an average of 70%. 73% of the preparations gave recoveries greater than 60%.

TABLE 1A

RECOVERY OF FROZEN-THAWED PLATELETS FROM PLATELET-RICH PLASMA[1]

| | FRESH PLATELETS | | | FROZEN-THAWED PLATELETS | | |
|---|---|---|---|---|---|---|
| Expt. | PRP (ml.) | PRP/μl (×10$^5$) | PRP TOTAL (×10$^{11}$) | PC/μl[2] (×10$^6$) | PC TOTAL (×10$^{11}$) | Recovery[3] % |
| 1 | 248 | 5.26 | 1.30 | 1.21 | 0.687 | 53 |
| 2 | 261 | 3.73 | 0.974 | 1.22 | 0.695 | 71 |
| 3 | 234 | 4.67 | 1.09 | 0.935 | 0.533 | 49 |
| 4 | 210 | 6.70 | 1.41 | 1.05 | 0.598 | 42 |
| 5 | 169 | 6.05 | 1.02 | 1.62 | 0.923 | 90 |
| 6 | 204 | 5.52 | 1.13 | 1.65 | 0.938 | 83 |
| 7 | 189 | 4.47 | 0.845 | 1.29 | 0.735 | 87 |
| 8 | 211 | 5.21 | 1.10 | 0.825 | 0.470 | 43 |
| 9 | 221 | 4.47 | 0.988 | 0.785 | 0.450 | 46 |
| 10 | 249 | 5.72 | 1.42 | 1.90 | 1.08 | 76 |
| 11 | 204 | 6.20 | 1.26 | 1.80 | 1.02 | 81 |
| 12 | 253 | 6.92 | 1.75 | 1.93 | 1.10 | 63 |
| 13 | 188 | 4.27 | 0.803 | 1.01 | 0.570 | 71 |
| 14 | 207 | 4.39 | 0.909s | 0.830 | 0.690 | 76 |
| 15 | 195 | 5.84 | 1.14 | 0.990 | 0.560 | 49 |
| 16 | 227 | 4.06 | 0.922 | 1.09 | 0.630 | 68 |
| 17 | 184 | 4.64 | 0.854 | 1.37 | 0.781 | 91 |
| 18 | 224 | 4.90 | 1.10 | 1.63 | 0.980 | 85 |
| 19 | 209 | 6.61 | 1.38 | 2.07 | 1.18 | 86 |
| 20 | 227 | 4.75 | 1.08 | 1.84 | 1.05 | 97 |
| 21 | 237 | 4.10 | 0.972 | 1.38 | 0.790 | 81 |
| 22 | 204 | 5.04 | 1.03 | 1.47 | 0.840 | 82 |
| 23 | 281 | 3.89 | 1.09 | 1.32 | 0.750 | 69 |
| 24 | 288 | 5.52 | 1.59 | 1.70 | 0.986 | 62 |
| 25 | 315 | 4.45 | 1.40 | 1.21 | 0.700 | 50 |
| 26 | 289 | 3.23 | 0.933 | 1.28 | 0.730 | 78 |
| | | | | | AVERAGE = | 70* |

[1]Abbreviations: PRP = platelet-rich plasma; PC = platelet concentrate
[2]The volume of PC varied from 44 to 60 ml, with an average of 57 ml.
[3]Recovery calculations reflect losses both in the processing and freeze-thawing procedures.
* Of the losses only 5 to 10% of the loss was due to the freezing, the balance being due to transfers.

In order to determine whether or not the procedure set forth above was repeatable different technicians were requested to conduct a series of 10 preparations following the identical procedure. The results which they obtained are set forth in Table 1B below. The recoveries ranged from 42% to 98% with an average of 71%, thereby confirming the results shown in Table 1A above.

TaBLE 1B

RECOVERY OF FROZEN-THAWED PLATELETS

| | FRESH PLATELETS | | | FROZEN-THAWED PLATELETS | | |
|---|---|---|---|---|---|---|
| Expt. | PRP[1] (ml.) | PRP/μl (×10$^5$) | PRP TOTAL (×10$^{11}$) | PC/μl[1] (×10$^6$) | PC TOTAL (×10$^{11}$) | Recovery[2] % |
| 1 | 253 | 8.96 | 2.27 | 1.72 | 0.960 | 42 |
| 2 | 270 | 7.98 | 2.15 | 3.01 | 1.70 | 79 |
| 3 | 238 | 7.98 | 1.90 | 3.33 | 1.86 | 98 |
| 4 | 209 | 10.6 | 2.22 | 2.94 | 1.38 | 62 |
| 5 | 228 | 7.55 | 1.72 | 1.79 | 0.789 | 46 |
| 6 | 240 | 5.95 | 1.43 | 1.89 | 1.10 | 77 |
| 7 | 259 | 6.72 | 1.74 | 1.89 | 1.14 | 66 |
| 8 | 248 | 12.3 | 3.05 | 4.61 | 2.67 | 88 |
| 9 | 288 | 6.34 | 1.83 | 2.43 | 1.36 | 74 |
| 10 | 250 | 5.38 | 1.35 | 1.84 | 1.04 | 77 |
| | | | | | AVERAGE = | 71 |

[1]Abbreviations: PRP = platelet-rich plasma; PC = platelet concentrate.
[2]Recovery calculations reflect losses both in the processing and freeze-thawing procedures.

In a separate group of 5 experiments, the average loss of platelets was found to be 29%, of which 16% was accounted for in the "platelet-poor plasma" and 8% left in the freezing solution supernatant liquid. The remainder (5%) was lost during transfer of platelets from the processing bag to the freezing bag. These three areas of losses accounted for approximately 97% of the total loss. These results confirmed that the process of the invention involving the glycerol (glycerol-glucose) treatment and freezing generally accounts for a loss of platelets not in excess of 15%, determined upon thawing of the frozen mass.

During these studies it was noted that the aggregation of thawed or reconstituted platelets can be prevented or minimized by complete removal of erythrocytes in the platelet-rich plasma or platelet concentrate. This can be accomplished by centrifugation of the platelet-rich plasma or platelet concentrate, resuspended in freezing solution. The centrifugation is typically conducted at 800 RPM for 2-3 minutes using a centrifuge such as a Sorval RC-3 centrifuge.

Platelet Size Distribution

A study of the platelet size distribution indicated that the size distribution of the platelets from fresh non-frozen platelet-rich plasma compared with those of thawed reconstituted platelets. A narrow peak that is seen only as a shoulder in the fresh platelets appears in the thawed samples below values of 1.5 $\mu^3$. Broader and often less sharply defined secondary peaks, with mean platelet size of 4 $\mu^3$, coincide with the primary peak of fresh platelet preparations. The number of large platelets make up a lesser proportion of the total thawed platelet population than in fresh platelets. Thus the platelets resulting from the freezing and thawing process display a pattern similar to those platelets in a platelet-rich plasma.

Serotonin Uptake

Table 2 set forth below illustrates the results of measurements of serotonin uptake by fresh and thawed platelets. These results show that the serotonin uptake by frozen-thawed platelets is some 90% of that obtained with fresh platelets, thereby serving as correlation of the statements above with respect to the lack of inactivation of the platelets.

TABLE 2

| | SEROTONIN UPTAKE[1] | |
|---|---|---|
| Platelet Preparation | Platelets/nm$^3$ | Uptake (%) |
| Fresh | 500,000 ± 105,000 (342,500 − 735,000) | 81.3 ± 5.8 (60.3 − 87.9) |
| Frozen-Thawed | 450,000 ± 165,000 (238,000 − 825,000) | 73.3 ± 10.9 (43.7 − 85.2) |

[1]The number of experiments in each group varied from 24 to 27.

Clot Retraction

The experiment to determine clot retraction compared the effect of fresh platelets with frozen-thawed platelets at various time intervals after thrombin addition. The concentration of platelets in each instance was the same. The effectiveness of frozen-thawed platelets in inducing clot retraction was similar to that of fresh platelets.

The above data indicates that by the use of a glycerol saline solution containing glucose, that an effective method for cryopreservation of platelets is provided. The use of these low concentrations of glycerol enables the introduction of platelets without any glycerol removal prior to or even subsequent to the thawing process.

The recovery rate of the intact platelets according to the present invention is quite high. Some 20% of the platelets are lost on the average due to transfers from bag to bag prior to freezing, whereas the freezing procedure itself accounts for only less than 10% of the overall loss. This means that notwithstanding the losses naturally occasioned from bag to bag transfer a minimum of platelets is lost due to the freezing process itself.

Functional integrity of the frozen-thawed platelets has been confirmed by the serotonin uptake, aggregation response test and the ability of the composition to cause clot retraction. The need for the enzyme apyrase in the test for aggregation underlies the presence of ADP in frozen-thawed platelet suspensions, contributed by damaged platelets and contaminating erythrocytes.

Although the size distribution patterns of fresh and frozen-thawed-reconstituted platelets differs, the pattern of the latter becomes comparable to that of the fresh platelets following removal of erythrocyte debris and platelet fragments.

The ability to use glycerol as a cryoprotective agent with glucose, in a simple process, is highly desirable inasmuch as osmotic stress obtained on removal of glycerol under the conditions of the present invention is not as severe as observed in high concentrations where the osmotic stress which could damage the platelets was presumably due to differences in permeability rates between the entry of water into the platelet and the exit of glycerol therefrom.

Since the platelets preserved by the method of the invention retain their integrity as determined by several in vitro criteria, this approach to freezing has important clinical aspects.

The foregoing description has described the freezing of blood platelets. These blood platelets can be derived from any human being. What is particularly contemplated is the freezing of the platelets from human blood and the administration of frozen and subsequently thawed human platelets into a human.

What is claimed is:

1. A process for preserving blood platelets which comprises:
  A. Contacting said platelets with an aqueous saline solution contaning 4 to 7 weight percent glycerol and 2 to 6 weight percent glucose, the glycerol being employed in at least a 5 : 1 volume solution to volume platelet ratio;
  B. Removing supernatant liquid;
  C. Concentrating platelets to about 20 mg platelet protein/ml;
  D. Thereafter freezing said platelets at a rate of at least 20° C per minute.

2. A process according to claim 1 wherein a mass results from step A and between steps A and B the resultant mass from step A is subjected to centrifugation to form a concentrated mass of platelets.

3. A process according to claim 2 wherein the concentrated mass is disposed in the form of a sheet and frozen in such form.

4. A process according to claim 3 wherein the platelets are frozen down to a temperature of at least −80° C.

5. A process according to claim 4 wherein the platelets are thereafter stored in liquid nitrogen at a temperature of −196° C.

6. A process according to claim 1 wherein the volume to volume ratio of saline solution to platelets is 10–45 : 1.

7. A process according to claim 1 wherein the salt concentration of said saline solution is 0.8 to 0.95 weight to volume percent.

8. A process according to claim 1 wherein the platelets treated in step A are in admixture with blood plasma and said platelets are concentrated in said plasma.

9. A process according to claim 1 wherein the platelet protein concentration is present in an amount of 10 to 20 mg protein per ml.

10. A process for preserving blood platelets which comprises:
   A. Contacting said platelets with an aqueous saline solution containing 4 to 7 weight percent glycerol and 2 to 6 weight percent glucose in at least 5 : 1 volume solution to volume platelet ratio;
   B. Removing supernatant liquid;
   C. Concentrating platelets to about 10–20 mg platelet protein per ml; and
   D. Thereafter freezing said platelets at a rate of at least 20° C per minute.

11. A process for preserving blood platelets which comprises:
   A. Contacting said platelets with an aqueous saline solution containing 4 to 7 weight percent glycerol and 2 to 6 weight percent glucose in at least 5 : 1 volume solution to volume platelet ratio;
   B. Removing supernatant liquid;
   C. Concentrating said platelets; and
   D. Thereafter freezing said platelets at a rate of at least 20° C per minute.

12. A process for preserving blood platelets which comprises:
   A. Contacting said platelets with an aqueous saline solution containing 4 to 7 weight percent glycerol in at least 5 : 1 volume solution to volume platelet ratio;
   B. Removing supernatant liquid; and
   C. Thereafter freezing said platelets at a rate of at least 20° C per minute.

13. A process according to claim 12 wherein said saline solution contains dextrose.

* * * * *